(12) United States Patent
Deflorian et al.

(10) Patent No.: US 9,717,813 B2
(45) Date of Patent: Aug. 1, 2017

(54) ELECTRICAL HEATING DEVICE FOR EVAPORATING VOLATILE SUBSTANCES WITH ADJUSTABLE EVAPORATION RATE

(75) Inventors: Stefano Deflorian, Trento (IT); Juan Antonio Gomez Gracia, Barcelona (ES); Cedric Morhain, Barcelona (ES)

(73) Assignee: ZOBELE HOLDING SPA, Trento (IT)

( * ) Notice: Subject to any disclaimer, the term of this patent is extended or adjusted under 35 U.S.C. 154(b) by 467 days.

(21) Appl. No.: 14/122,295

(22) PCT Filed: Jun. 11, 2012

(86) PCT No.: PCT/EP2012/060981
§ 371 (c)(1),
(2), (4) Date: Nov. 26, 2013

(87) PCT Pub. No.: WO2012/171869
PCT Pub. Date: Dec. 20, 2012

(65) Prior Publication Data
US 2014/0093224 A1     Apr. 3, 2014

(30) Foreign Application Priority Data

Jun. 13, 2011 (EP) .................................... 11169658

(51) Int. Cl.
*A61L 9/03* (2006.01)
*A01M 1/20* (2006.01)

(52) U.S. Cl.
CPC ........... *A61L 9/037* (2013.01); *A01M 1/2077* (2013.01); *A61L 9/03* (2013.01); *A61L 9/035* (2013.01)

(58) Field of Classification Search
CPC ........ A01M 1/2077; A61L 9/03; A61L 9/037; A61L 9/035
USPC ................. 338/117, 129, 133, 171, 173, 178
See application file for complete search history.

(56) References Cited

U.S. PATENT DOCUMENTS

| 3,109,754 | A | * | 11/1963 | Tielens | .................. | H01C 1/034 |
| | | | | | | 338/262 |
| 3,211,031 | A | * | 10/1965 | Martin | ..................... | H01B 1/00 |
| | | | | | | 29/620 |
| 3,617,976 | A | * | 11/1971 | Campbell | .............. | H01C 10/44 |
| | | | | | | 338/133 |

(Continued)

FOREIGN PATENT DOCUMENTS

| EP | 0942648 | 9/1999 |
| EP | 0962132 | 12/1999 |

(Continued)

OTHER PUBLICATIONS

International Search Report for International PCT Application No. PCT/EP2012/060981, mailed Oct. 30, 2012.

*Primary Examiner* — David Angwin
*Assistant Examiner* — Amit K Singh
(74) *Attorney, Agent, or Firm* — Pearl Cohen Zedek Latzer Baratz LLP

(57) ABSTRACT

An electrical heating evaporator for evaporating active substances such as perfumes and/or insecticides, in which the evaporation rate regulator includes an electrical heater resistor for which the power supplied is regulated through a potentiometer constructed on a printed circuit board. The evaporation rate can be adjusted for a wide variety of types of chemical substances, without the need of substantially modifying the design of the device.

12 Claims, 17 Drawing Sheets

(56) References Cited

U.S. PATENT DOCUMENTS

| | | | | |
|---|---|---|---|---|
| 4,237,442 A * | 12/1980 | Carter | ............... | H01C 1/142 |
| | | | | 338/138 |
| 4,435,691 A * | 3/1984 | Ginn | ............... | H01C 10/04 |
| | | | | 338/125 |
| 4,559,515 A * | 12/1985 | Takezawa | ........... | H01C 10/44 |
| | | | | 338/128 |
| 5,339,065 A | 8/1994 | Slenker | | |
| 6,141,496 A | 10/2000 | Sundberg et al. | | |
| 6,661,967 B2 | 12/2003 | Levine et al. | | |
| 2002/0131888 A1* | 9/2002 | Zobele | ............ | A01M 1/2077 |
| | | | | 422/5 |
| 2004/0033067 A1 | 2/2004 | He et al. | | |
| 2006/0193611 A1 | 8/2006 | Ruiz Ballesteros et al. | | |
| 2007/0280653 A1* | 12/2007 | Viera | ............... | A01M 1/2072 |
| | | | | 392/395 |
| 2009/0224064 A1* | 9/2009 | Brodbeck | ........ | A01M 1/2077 |
| | | | | 239/6 |

FOREIGN PATENT DOCUMENTS

| | | |
|---|---|---|
| EP | 1064957 | 1/2001 |
| EP | 1247446 | 10/2002 |
| EP | 1358891 | 11/2003 |
| WO | WO 2004/020006 A1 | 3/2004 |

\* cited by examiner

FIG. 6a
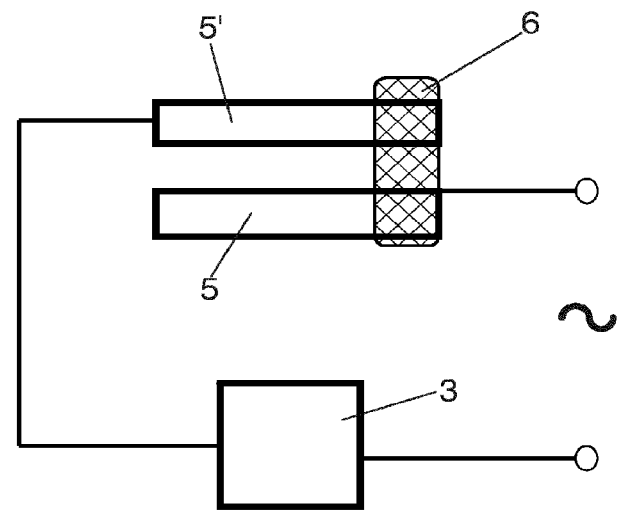
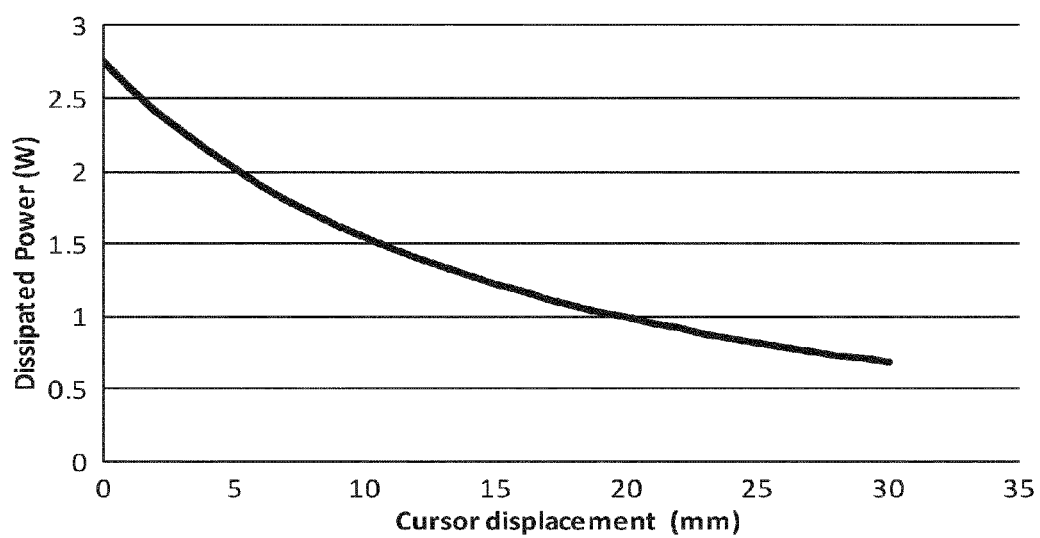
FIG. 6b

FIG. 7a
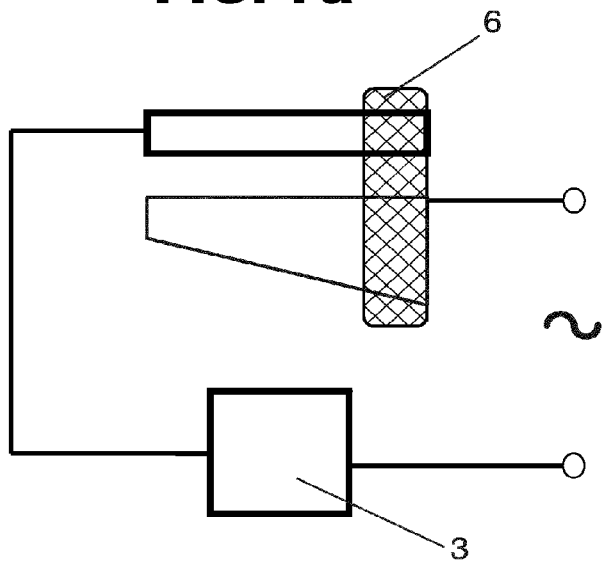
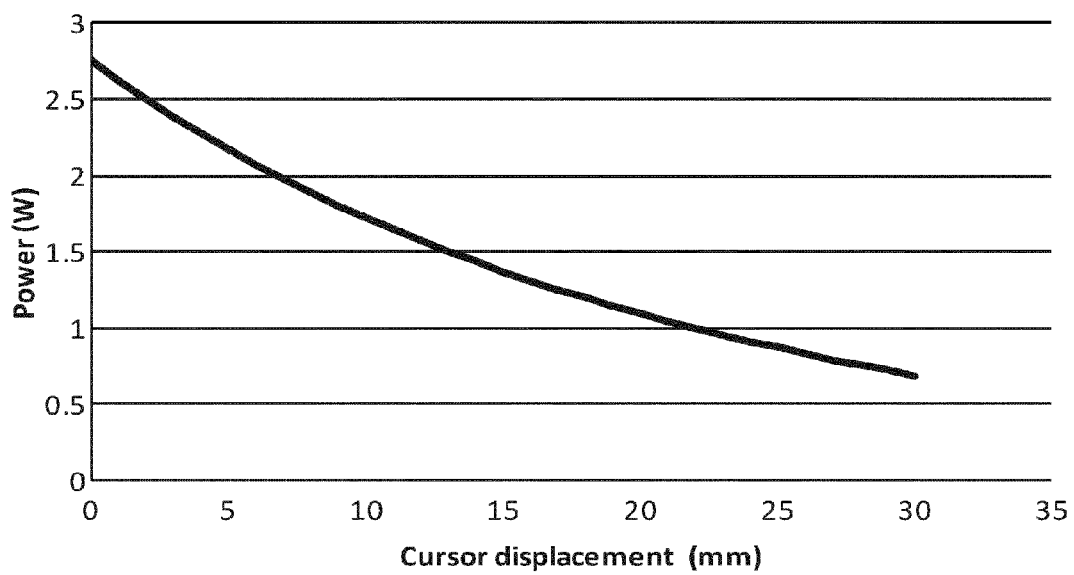
FIG. 7b

FIG. 8a
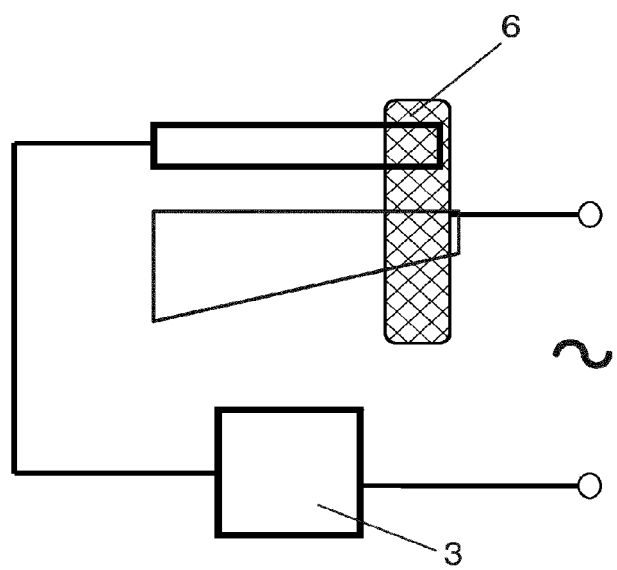
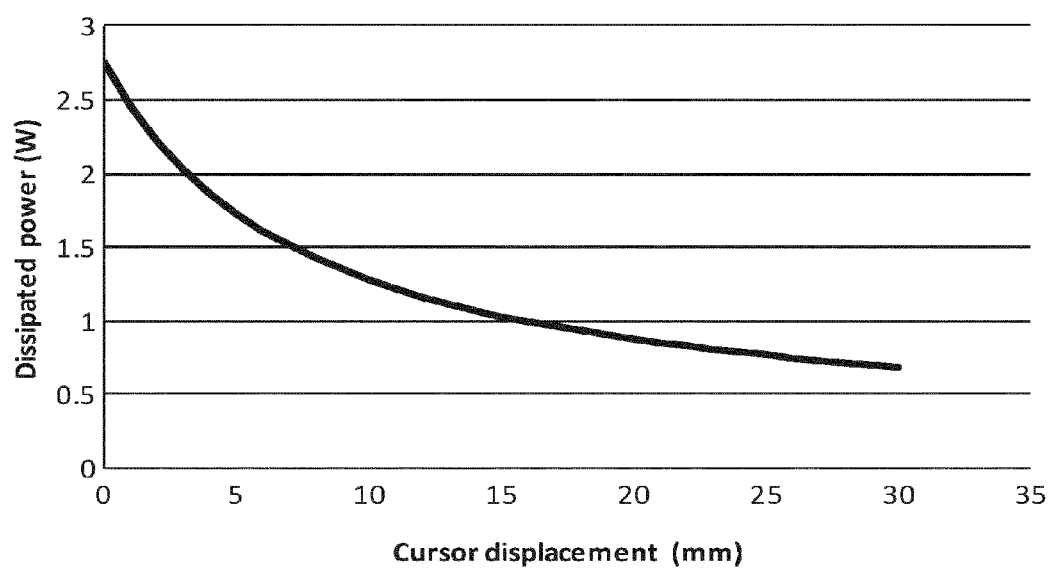
FIG. 8b

FIG. 9a
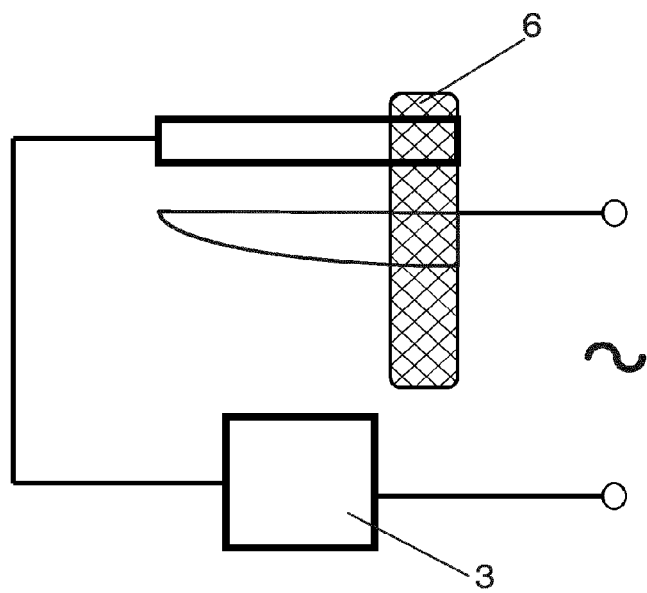
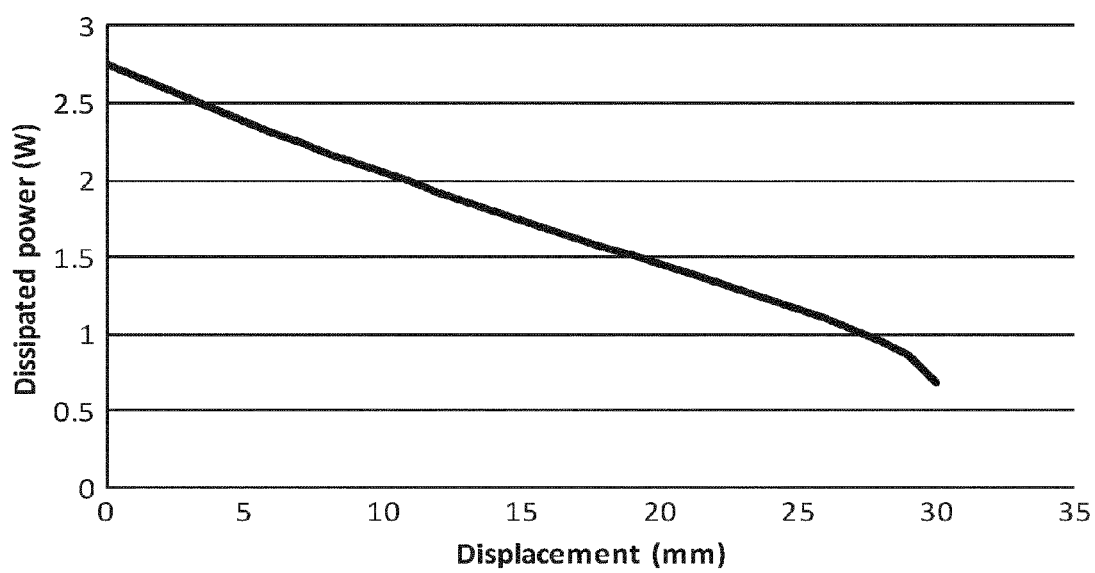
FIG. 9b

FIG. 10a
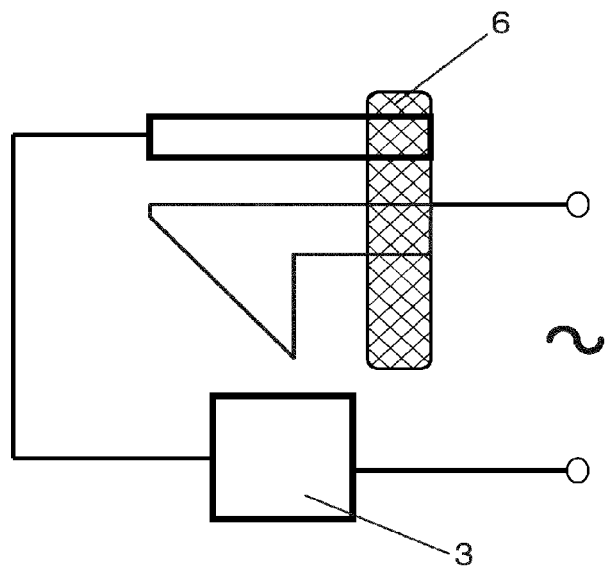
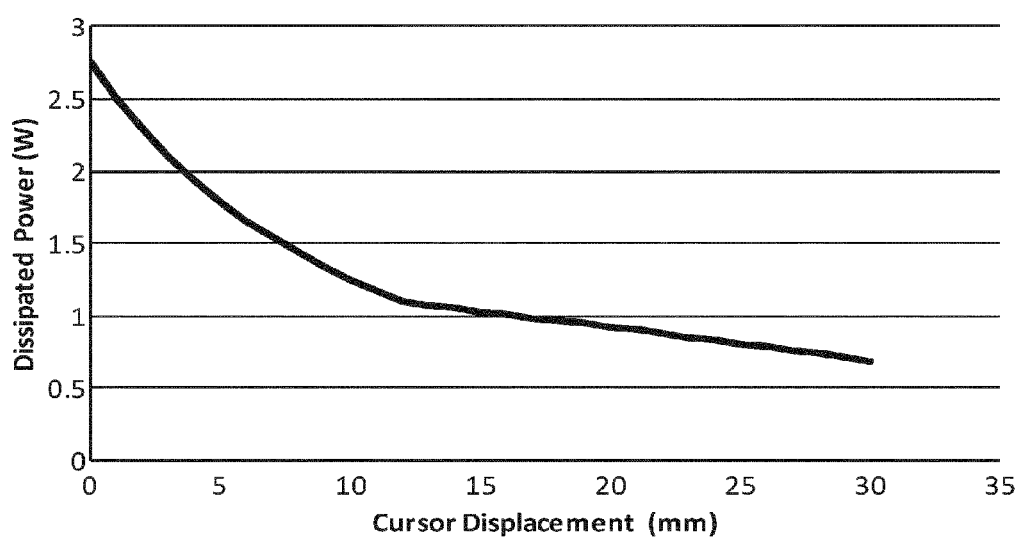
FIG. 10b

ELECTRICAL HEATING DEVICE FOR EVAPORATING VOLATILE SUBSTANCES WITH ADJUSTABLE EVAPORATION RATE

CROSS-REFERENCE TO RELATED APPLICATIONS

This application is a National Phase Application of PCT International Application No. PCT/EP2012/060981, International Filing Date Jun. 11, 2012, claiming priority of European Patent Application No. 11169658.9, filed Jun. 13, 2011, which is hereby incorporated by reference.

OBJECT OF THE INVENTION

The present invention relates in general to apparatus for evaporating volatile substances.

More in particular, the invention provides an electrical heating evaporator for evaporating active substances such as perfumes and/or insecticides, in which the means for regulating the evaporation rate, can be adjusted for a wide variety of types of active substances, without the need of substantially modifying the design of the device in the manufacturing process.

BACKGROUND OF THE INVENTION

Evaporator devices for volatile substances are very well-know, for diffusing air fresheners, pesticides or similar chemical substances.

Two basic types of such heating devices are manufactured: a first type in which heating of a support plate impregnated with the desired active ingredient is performed; and a second type in which a wick is provided, said wick being partially immersed in a small bottle containing said substances in liquid form and conveying, by means of capillarity, the essence into the vicinity of a heating element.

Evaporating devices with electrical heater to activate evaporation are known for many years. Many of them present the advantage of having regulation means in order to adjust the evaporation rate.

Most of these regulation means are dealing with mechanical constructions that affect the heat transfer from the heater to the wick:

by varying the position between wick and heater, see for example patents EP-0942648, EP-0962132.

by varying the air flow around the wick (chimney effect), see for example patents EP-1064957 and EP-1358891.

In some other cases, electrical constructions are used to adjust the power dissipated in the heater, as described for example in the U.S. Pat. No. 6,661,967. In others, temperature of the wick can be adjusted by selectively activating several heaters placed around the wick, see for example European Patent EP-1247446B1.

However, each specific chemical active ingredient to be vaporised, and more specially perfumes, have an intrinsic working evaporating range temperature. For an optimum operation, regulation of the maximum and minimum temperature should be within this intrinsic working evaporating range of the particular chemical active ingredient to be evaporated.

In fact, regulation of the evaporation rate of perfume by changing applied heat is not a trivial question: due to the fact perfumes are very complex mixtures of a high number of different chemical components, each of them having its own volatility behaviour, any change of temperature will modify the composition of the vapours emanated. Thus the maximum-minimum range of regulation should be controlled in order to guarantee the evaporation conditions do not results in an unacceptable modification of the olfactory note of the perfume.

Current regulations means present the following drawbacks:

(i) For solutions where regulation is achieved through the mechanical construction, it is not possible to change the regulation range (meaning wick temperature and max and min value) without changing the mechanical construction of the device, which means that different designs or variants of the components of the device have to be manufactured, for which different moulds and manufacturing tools have to the produced for the different parts involved. The corresponding economic investment is generally not possible to assume.

Therefore, a particular evaporator device can only be used with a limited variety of perfume compositions, thus, it is the perfume chemical composition that has to be adapted to the regulation capabilities of the device and not the opposite.

(ii) For solutions where regulation is done by electrical means, the minimum and maximum temperature can be set to the correct value for each perfume by changing the ohmic value of electrical resistors used in the device. However, this kind of regulation only allow a limited number of values (2, max 3 according prior art). This lack of freedom for the consumer can lead to insatisfation as minimum performance can be too low and maximum too high, with no possibility for an intermediate value.

Therefore, there is no solution in the prior art providing gradual regulation between minimum and maximum evaporation rate, with the possibility of adjusting the regulation range of the same evaporator device (without modifying its physical design), for a wide variety of perfumes.

DESCRIPTION OF THE INVENTION

One object of this invention, is to solve the previously described drawbacks of the prior art, in a simple and economic manner.

The present invention refers to an electric evaporator device for evaporating and diffusing volatile substances, which comprises at least one electric heating resistor to heat a volatile substance for enhancing its evaporation.

The electric power supplied to the heating resistor, is regulated through a potentiometer constructed on any solid surface of the device suitable for receiving the tracks of the potentiometer. For example, said solid surface may be obtained by solid substrate provided for that purpose in the device. Said solid substrate may be made of a porous material, so that the porous substrate may act as a wick, to convey a liquid volatile substance to the proximity of the heating resistor. Said solid substrate may also be made of a non porous material, on which surface capillar means have been patterned in order to transport the liquid on the surface of the substrate up to the proximity of the heating resistor.

The solid substrate may also be formed by a printed circuit board.

More in detail, the electric evaporator device comprises at least one heating resistor arranged in the device for heating a volatile substance carrier when this carrier is coupled with the device, and a potentiometer constructed on a printed circuit board, so that said potentiometer is electrically associated with said heating resistor for regulating the electric current passing through the resistor, and regulating thereby the intensity degree of the evaporation.

Preferably, the potentiometer is a planar potentiometer having two conductive tracks and a cursor arranged for sliding along said tracks connecting them. Said conductive tracks are formed as printed tracks of a conductive surface of a general purpose printed circuit board of the device, in which other electronic components necessary for the operation of the device are also installed. Therefore, said PCB should not be confused with a PCB used specifically to construct a conventional potentiometer.

The fact that the heater resistor can be selected (in the manufacturing process), from an infinite number of ohmic values, and that on-PCB potentiometer pattern can be modified on-demand, allow a precise definition of the mean value of the temperature on the wick and also of the maximum and minimum value, with all possible values in-between, in order to adjust it to a particular fragrance volatility characteristics.

The effect of this, is that in the present invention, is very simple to select a desired ohmic (resistive) value of the potentiometer from an infinite number of ohmic values, simply by select during the manufacturing process of the device, a particular material, shape and/or dimensions of the tracks of the potentiometer during its manufacture.

DESCRIPTION OF THE DRAWINGS

To complete the description that is being made and with the object of assisting in a better understanding of the characteristics of the invention, in accordance with a preferred example of practical embodiment thereof, is a set of drawings wherein by way of illustration and not restrictively, the following has been represented:

FIGS. 6 to 10.—shows several alternatives for configuring the tracks of the planar potentiometer, in order to obtain a desired resistive pattern of the same. Each figure shows an electric diagram of the planar potentiometer (above), and the corresponding diagram (below) of the regulation pattern (dissipated thermal power) obtained for that particular configuration of the tracks of potentiometer.

As it can be observed in these figures, simply by modifying the material, shape, width and/or thickness of at least one of the tracks, the shape of dissipated power graph, is modified at will in a very simple manner.

PREFERRED EMBODIMENTS OF THE INVENTION

Figure 1A:
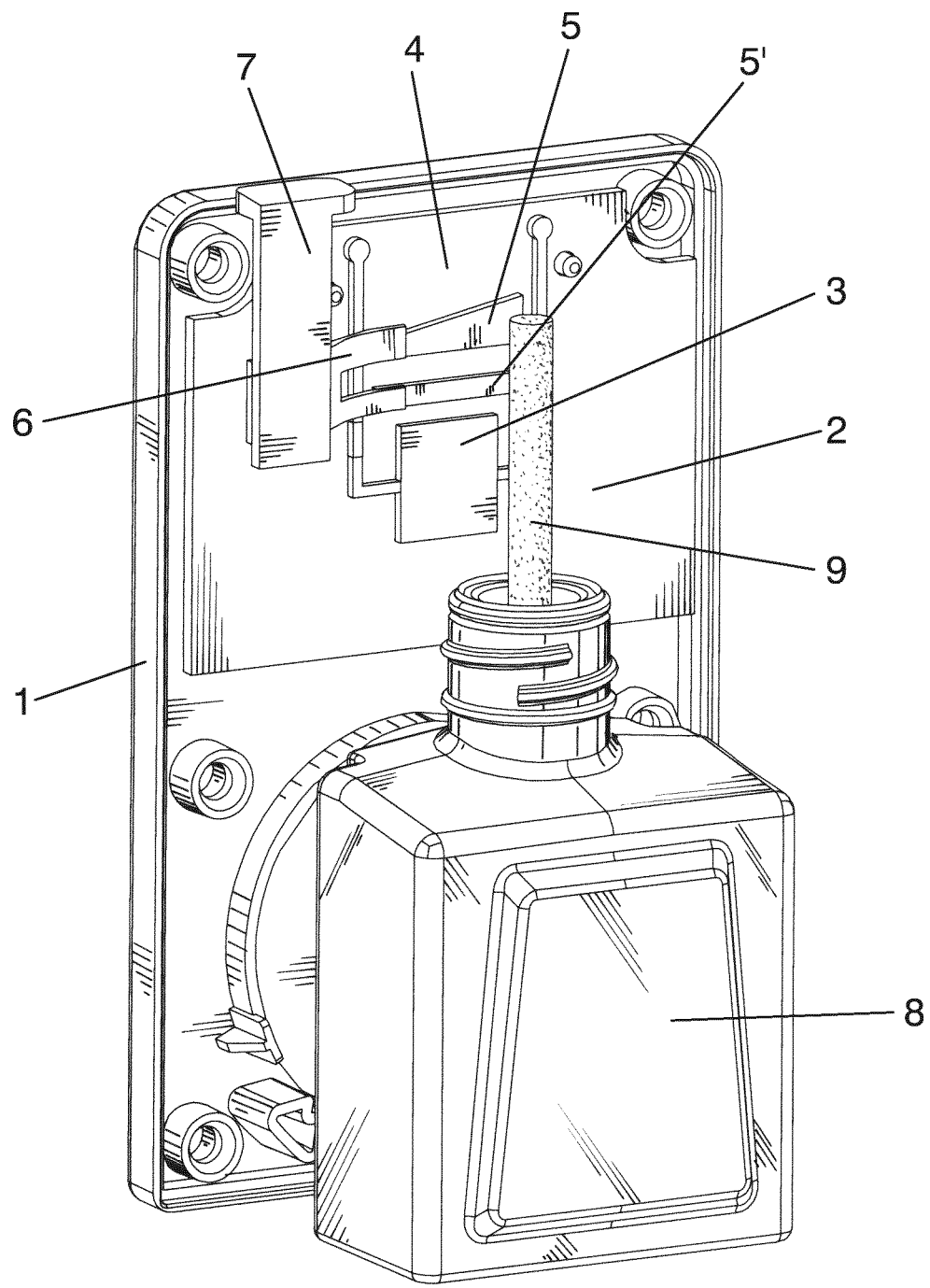
FIG. 1.—shows two perspective views (a,b), of one exemplary embodiment of the invention with a single heating resistor and potentiometer. Only some components of the device have been represented for the shake of clarity of the illustration, however, it would be obvious for the skilled person that other components, such as an electric plug for connecting the device to the mains supply, and a complete casing for receiving the container of the volatile substance, would be incorporated in a commercial product.
Figure 1B:
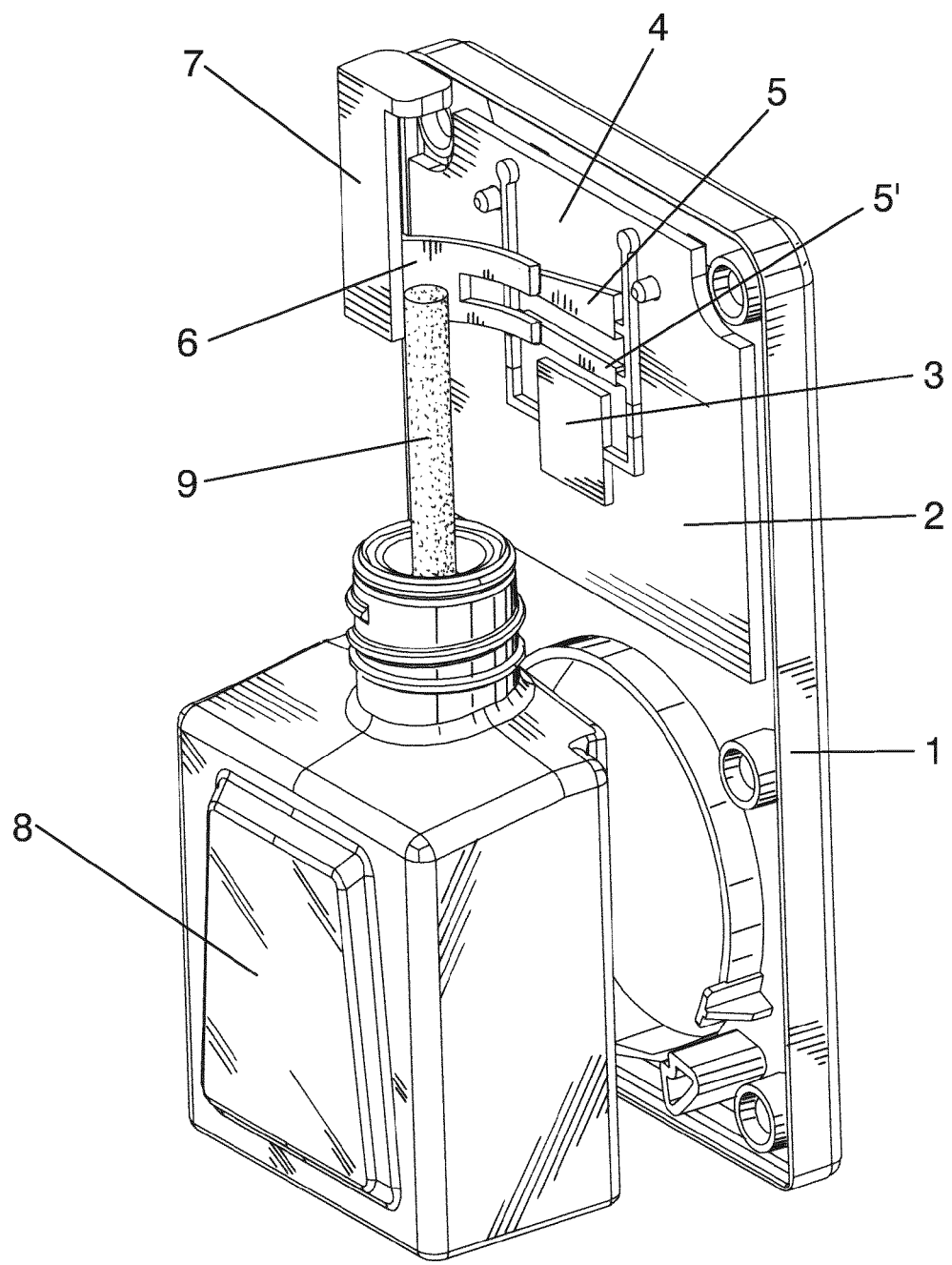

FIG. 1 shows an electrical heating device in accordance with the invention, comprising one heating resistor (3) arranged in the device for heating a volatile substance carrier, and a potentiometer (4) which is electrically associated (connected) with said heating resistor (3) in a known manner for regulating the electric current passing through the resistor (3), in order to manually regulate the evaporation rate of the volatile substance to be diffused to the air.

The heating resistor (3) and the potentiometer (4) are mounted on a face of a PCB (printed circuit board) (2) which is an integral part of the device, for example the PCB (2) may be fixed internally to a part of the casing (1) of the device.

The resistor (3) and potentiometer (4) are mounted on the same face (front face) of the PCB, directly facing the wick (3), as shown in the figures of the application.

The evaporated substance emanating from the wick, may reach the PCB and condensate thereon, in which case a liquid path can be formed between both tracks and short-circuit them.

To prevent this, in an alternative embodiment, the potentiometer (4) is arranged on the back face (not shown) of the PCB, in order to be physically isolate the potentiometer from the wick and prevent the risk that the tracks (5,5') are short-circuited by the evaporated substance reaching the tracks.

There are other printed tracks on the PCB connecting in series the heating resistor and the potentiometer, these elements being feed by the mains supply.

Also in order to prevent damages and short-circuits, the conductive tracks (5,5') are covered by an electrical conductive protective lacquer for chemically isolating the tracks.

Preferably, the heating resistor (3) is a planar resistor mounted on the PCB, and it is implemented as a metal oxide resistor. Alternatively, the heating resistor (3) may have another configuration, and it can be mounted on another part of the device.

In this embodiment, the potentiometer (4) is a planar potentiometer, and comprises two parallel and separated elongated tracks (5,5') which are constructed as conductive tracks of the PCB (2) by a know manufacturing process.

These tracks can be made of any material with the correct conductive properties to obtain a flat film deposited on the PCB, with the target overall maximal resistance value of the potentiometer. Preferably, tracks of the potentiometer are made of a polymeric conductive material, that is applied for example by screenprinting on the PCB. But it is clear that any other material having suitable conductive properties and any other process to correctly apply this material in a flat shape could be used for the same purpose in the present invention.

Advantageously in one embodiment of the invention, one of the tracks of the potentiometer (base track) has a very low resistance value (0 value) and the overall resistance value of the potentiometer, is achieved through the resistance of the other track (main track). This can be obtained by using two different conductive materials having very low resistivity for the base track and higher resistivity for the main track. This can be also obtained by using the same conductive material for both tracks, but applying it with a thicker and/or wider pattern for the base track and a thinner and/or narrower pattern for the main track.

Advantageously, the overall resistance of the main track, for example may have a resistance value in the same magnitude order than the heater resistance value.

Advantageously, the overall resistance of the main track for example may have a resistance value between 0.5 and 2 time the heater resistance value.

Advantageously, the overall resistance of the main track for example may have a resistance value equal to the heater resistance value.

Preferably, the heater resistance value would be in a range suitable to dissipate heating energy between 0.5 and 5 W. Nevertheless, the system of the present invention would also works correctly for values outside this range.

A cursor (6) made of an electrically conductive material, is configured to slide along the two tracks (5,5') simultaneously to adjust the resistive value of the potentiometer in a known manner.

A sliding knob (7) is joined to the cursor (6) and it is accessible from the outside of the device, so that an user can manually move the cursor and select thereby a desired evaporation rate.

The tracks of the planar potentiometer (4) are configured in order to obtain a desired specific profile of evolution of heat dissipated in the heater resistance (see FIGS. 6 to 10), while the cursor is progressively displaced from minimum regulation position to maximum regulation position, in order to translate the linear movement of the cursor in a non-linear variation of the dissipated power, to compensate the fact that the relationship between temperature and evaporation rate is not linear.

To implement this planar potentiometer (4) in a simple manner, the width of one of the tracks increases from one end of the track to the other end, so that one end has a higher ohmic value than the other end:

Consequently, this track has the shape of a triangle or a ramp.

The potentiometers could also consist of a conventional cylindrical potentiometers.

Preferably, the volatile substance carrier is a porous wick (9) having a part immersed in a liquid volatile substance (not shown) contained in a container (8), whereas the other part of the wick protrudes outside the container (8). The volatile substance composition may include a perfume and/or insecticide chemical product.

In operation, the heating resistor (3) is arranged to heat an upper part of the wick to enhance evaporation.

As shown in the figures, the wick (9) is a cylindrical body vertically arranged in the device. The PCB (2) is a planar body also vertically arranged, and parallel to the longitudinal axis of the wick. One effect of this arrangement, is that the device is compact and has a thin profile.

Figure 2A:
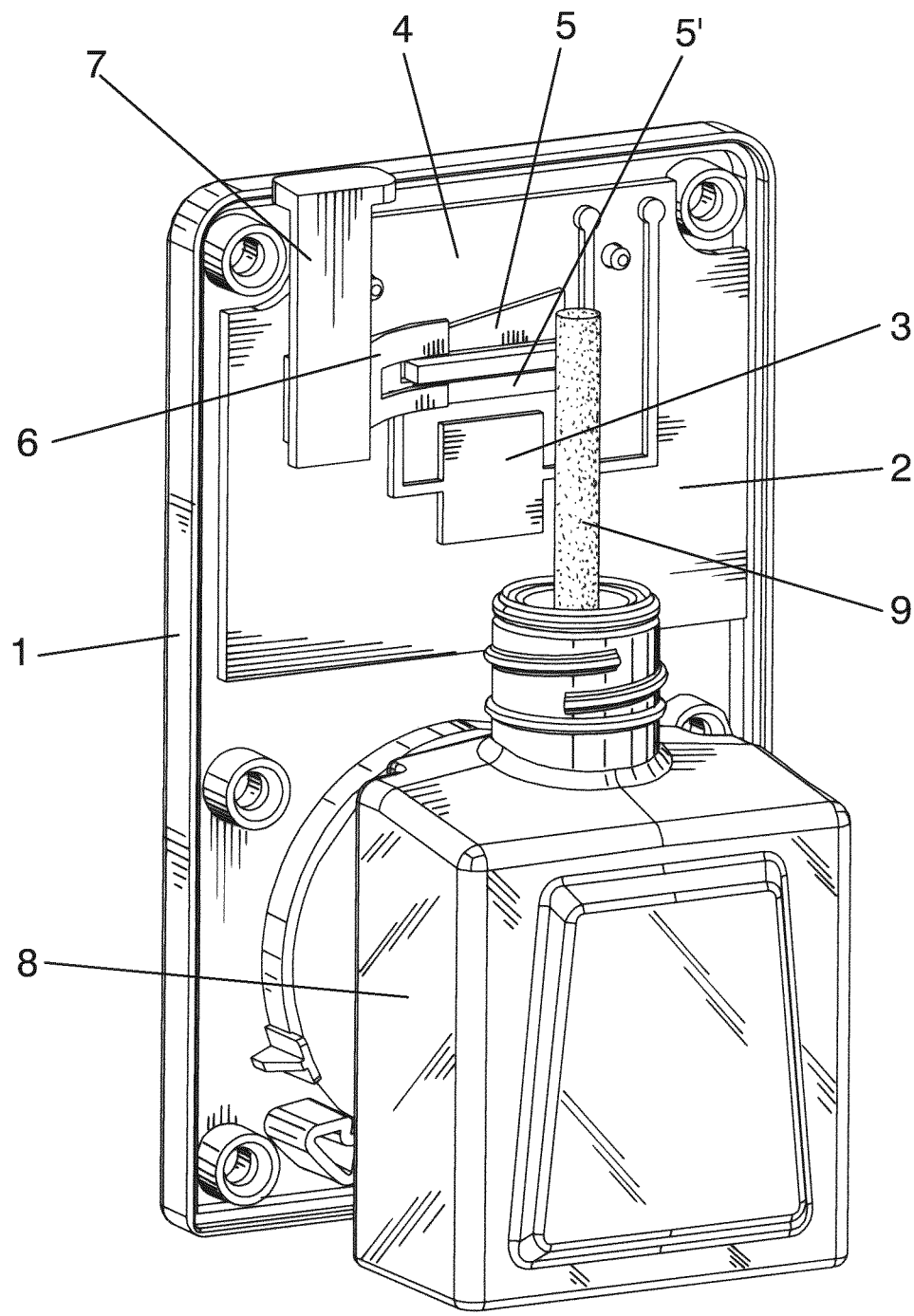
FIG. 2.—shows, in a similar representation than FIG. 1, another embodiment of the invention in which a separating hole is provided in the printed circuit board for separating the two tracks of the potentiometer.
Figure 2B:
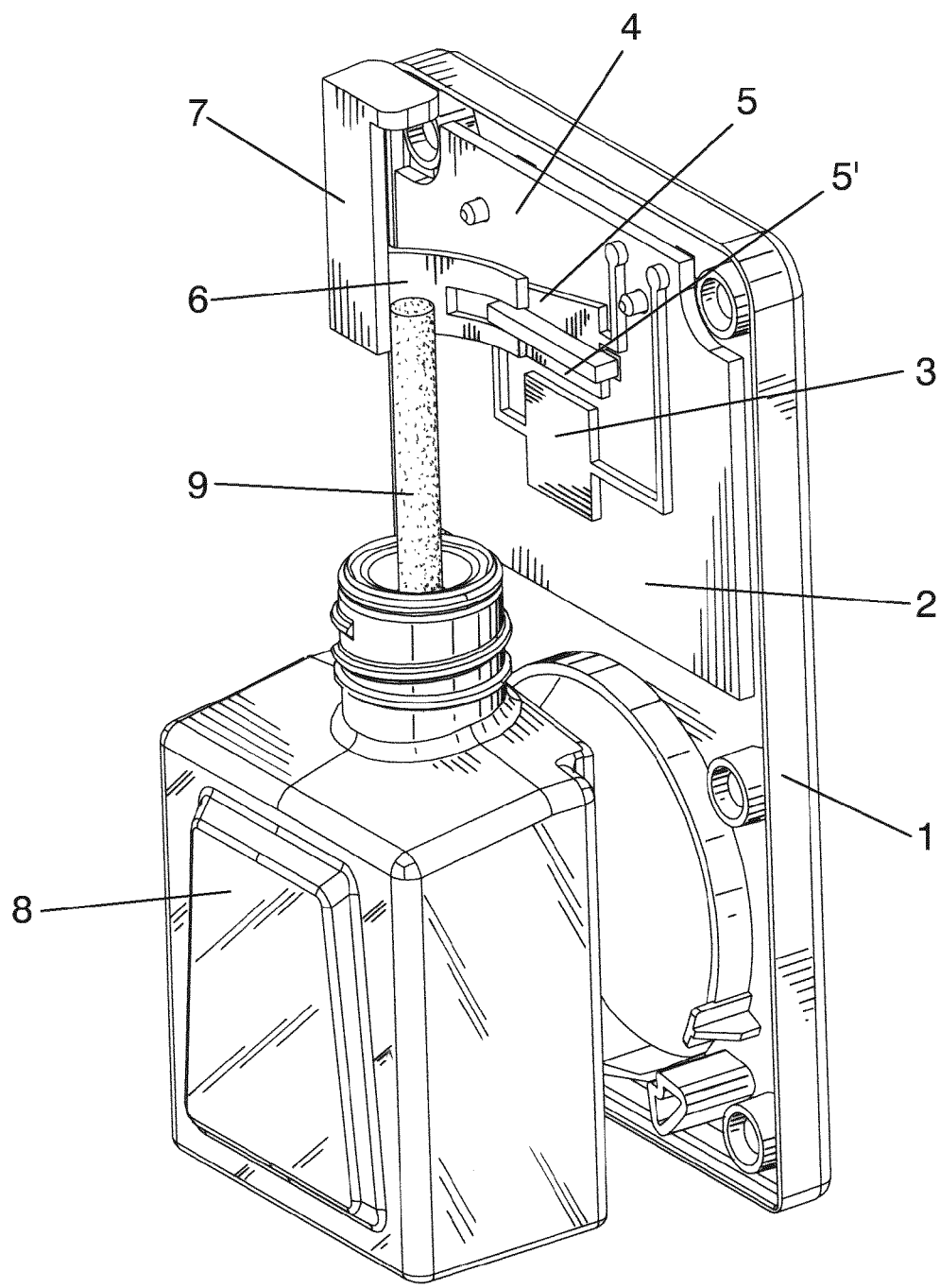
Figure 2C:
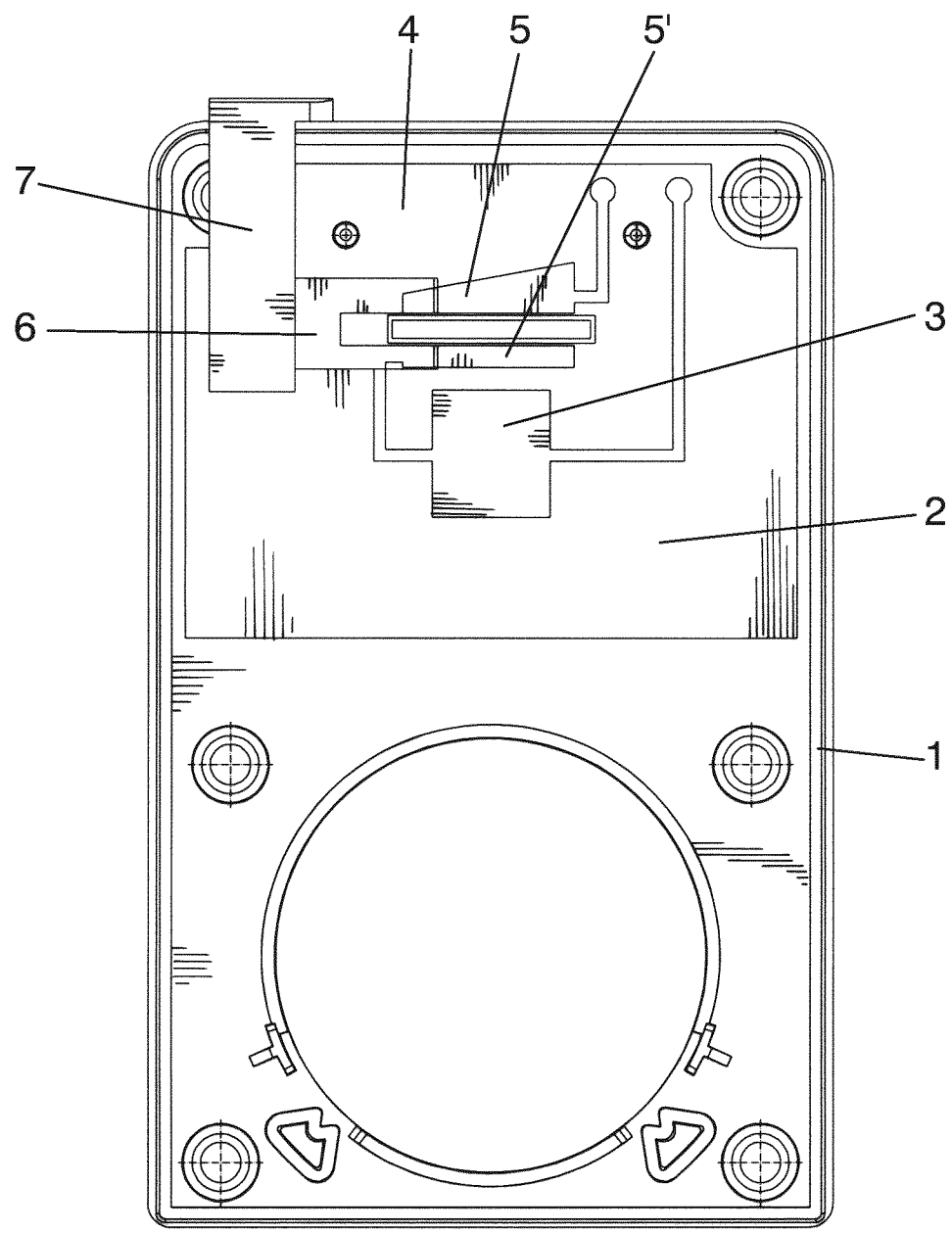

In the embodiment of FIG. 2, a separating hole (10) is provided perforating the PCB (2) in between the two parallel tracks (5,5'), in order to physically isolate the two tracks and prevent that condensation of the evaporated product short-circuit the tracks (5,5'). The hole (10) passes through the core substrate of the PCB and communicates both faces of the same.

Figure 3:
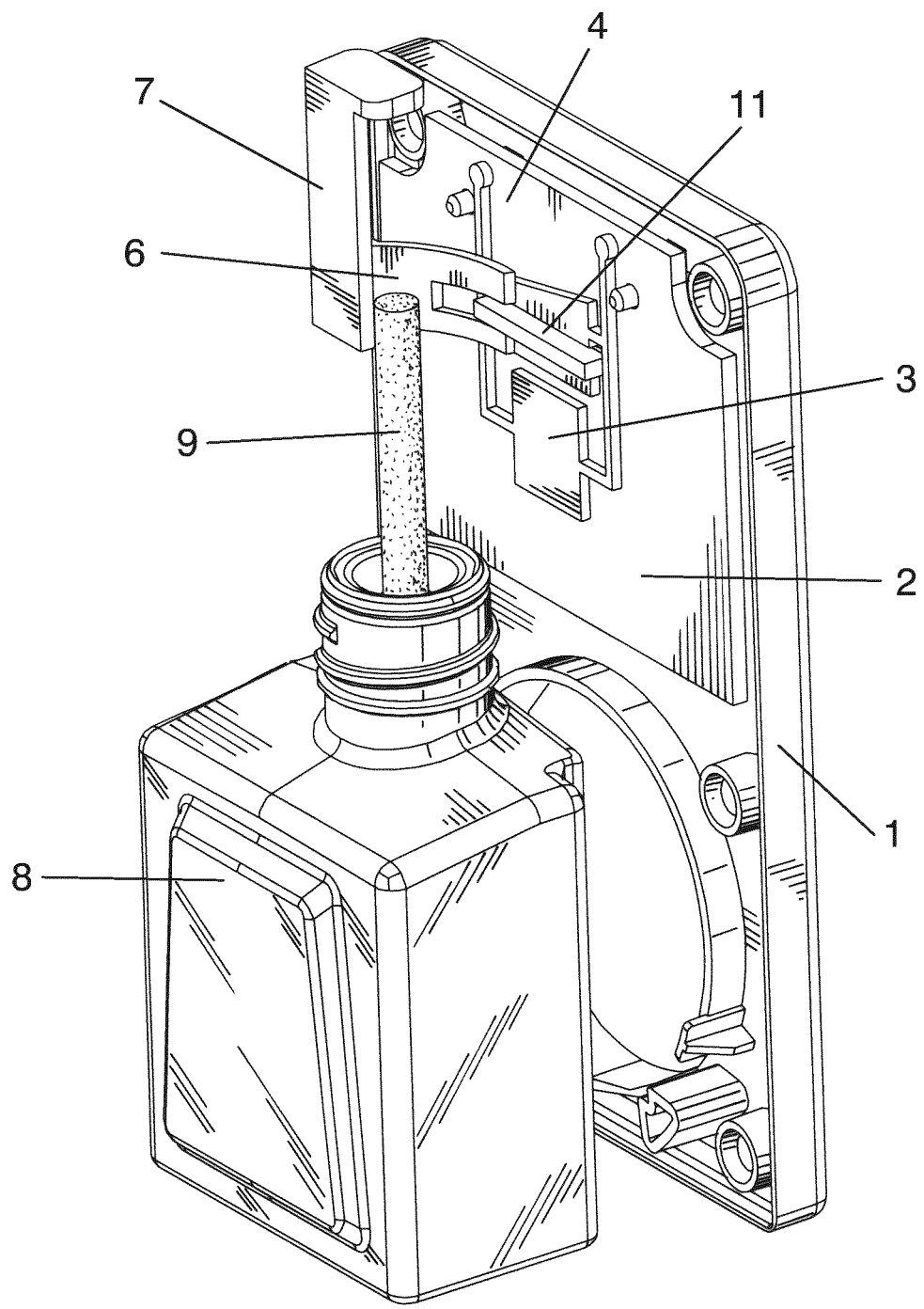
FIG. 3.—shows, in a similar representation than FIG. 1, another embodiment of the invention in which a separating wall is provided in the printed circuit board for separating the two tracks of the potentiometer.
Figure 4A:
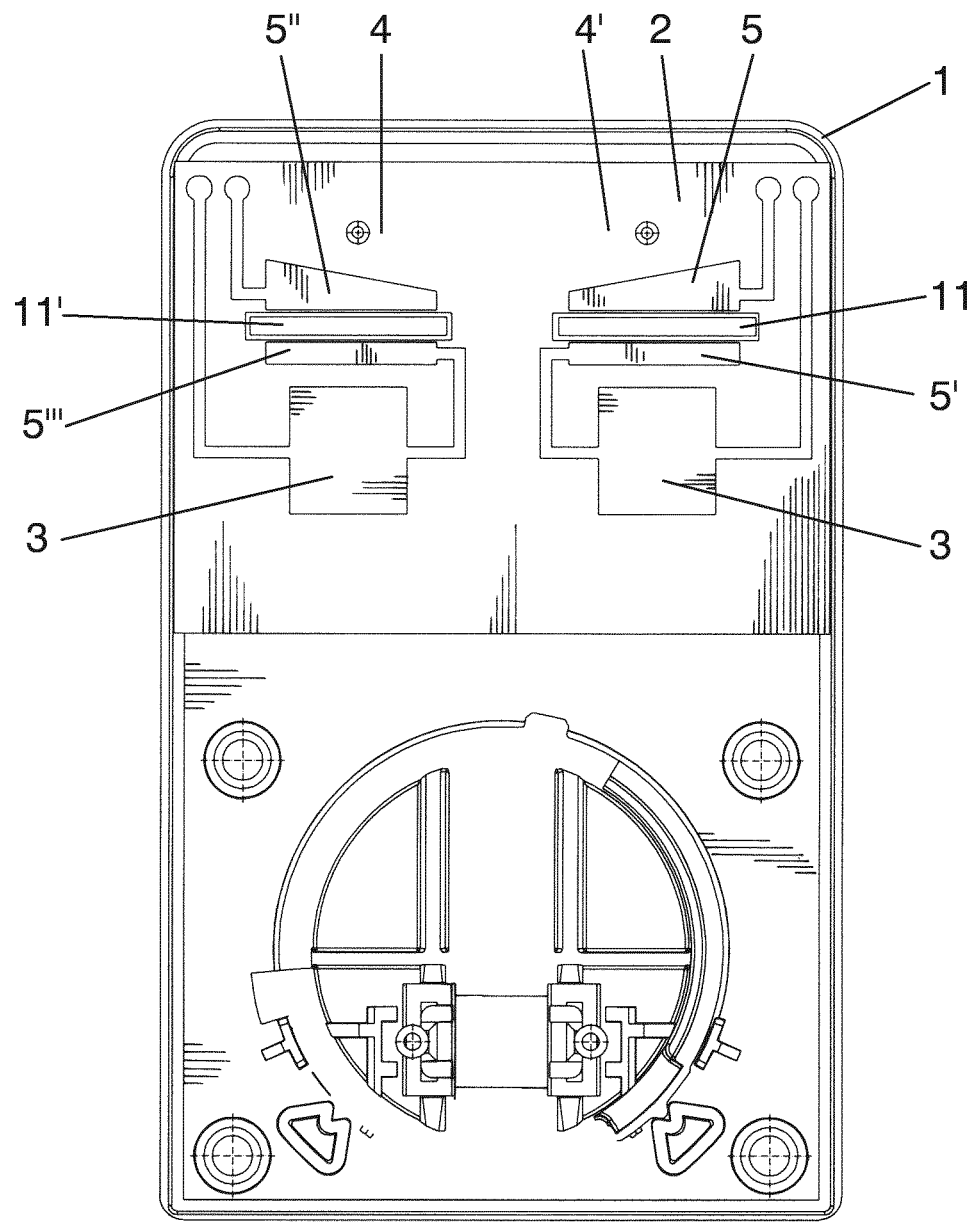
FIG. 4.—shows two front elevational views (a,b) and one perspective view (c) of a multifragrance embodiment of the invention. Drawing (d) is a magnified detail of a part of drawing (c).
Figure 4B:
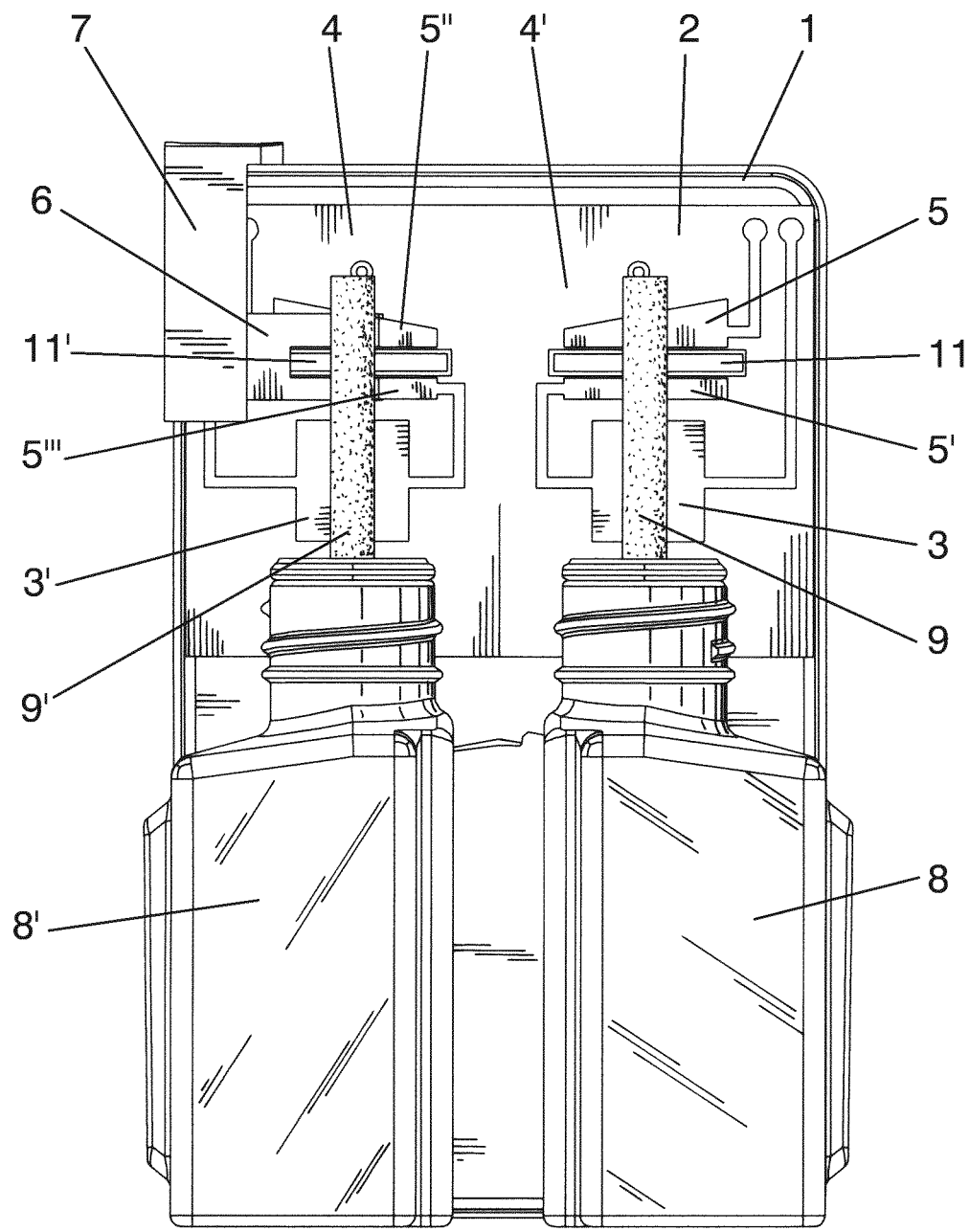
Figure 4C:
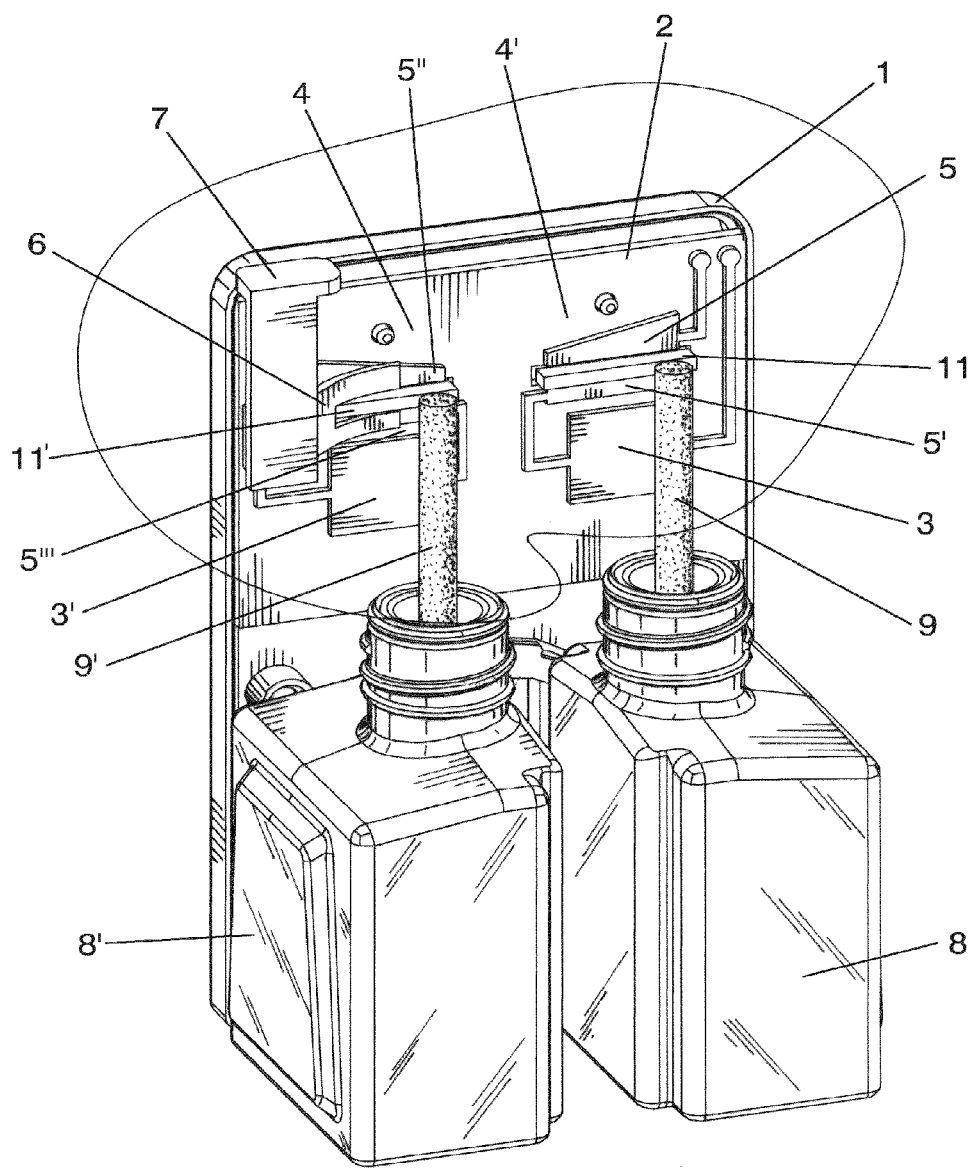
Figure 4D:
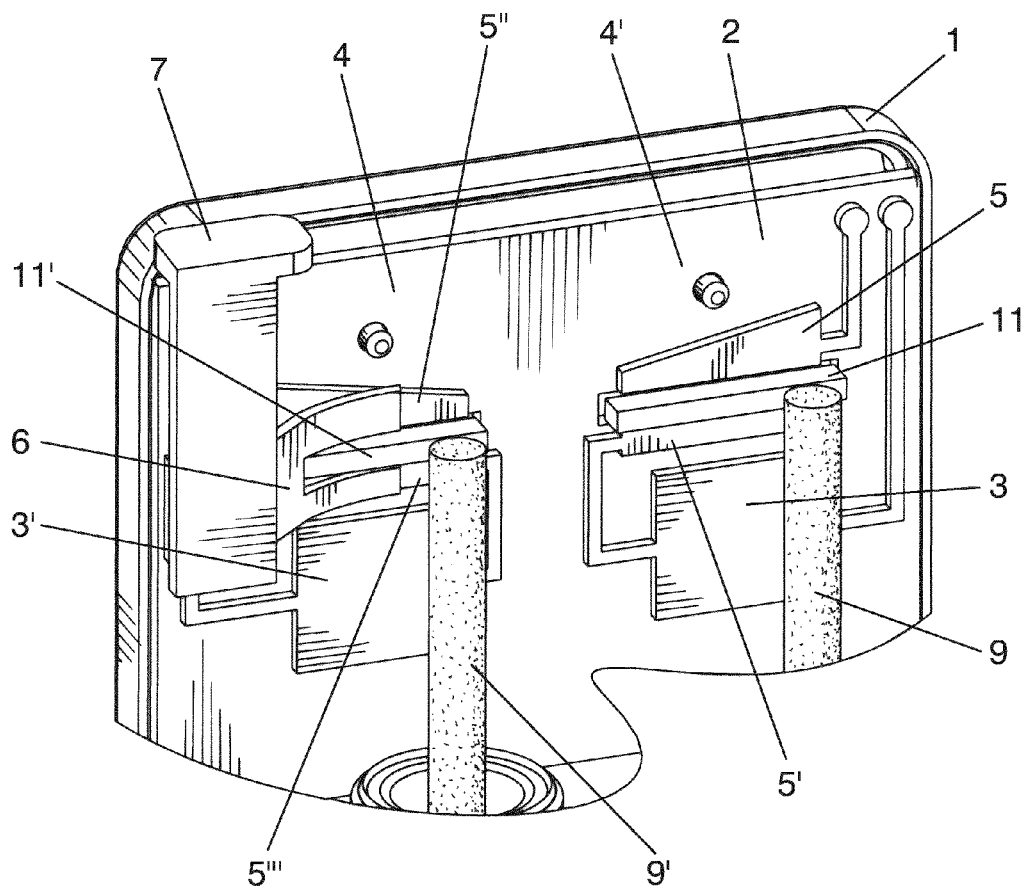

Alternatively, as shown in FIG. 3, a separating wall (11) is provided in between the tracks (5,5') and extending from the printed circuit board also for separating the two tracks of the potentiometer.

FIG. 4 shows a multifragrance emission device, in which the evaporation of the differences fragrances is alternated. The device comprises: two wicks (9,9') and associated containers (8,8'), two corresponding heating resistors (3,3'), two potentiometers (4,4'), and two separating walls (11,11').

A single cursor (6) is provided in common for regulating the resistive value of the two potentiometers (4,4'), which in this case, are arranged side by side, so that the cursor (6) slides only on the tracks of one potentiometer at a time, to set a resistive value only for one potentiometer, whereas the other potentiometer is open.

The effect of the embodiment of FIG. 4, is that a progressive switching in the diffusion of two perfumes without mixing them, is obtained. While cursor (6) passes from left to right as shown in FIG. 4, along the potentiometer (4), the evaporation rate of a first perfume (evaporated from wick (9')) is progressively decreased down to zero emission, and then, as the cursor (6) slide along the potentiometer (4"), the evaporation rate of a second perfume (evaporated from wick (9)) is progressively increased up to maximum level.

It is possible to have a zero emission position or not.

Figure 5A:
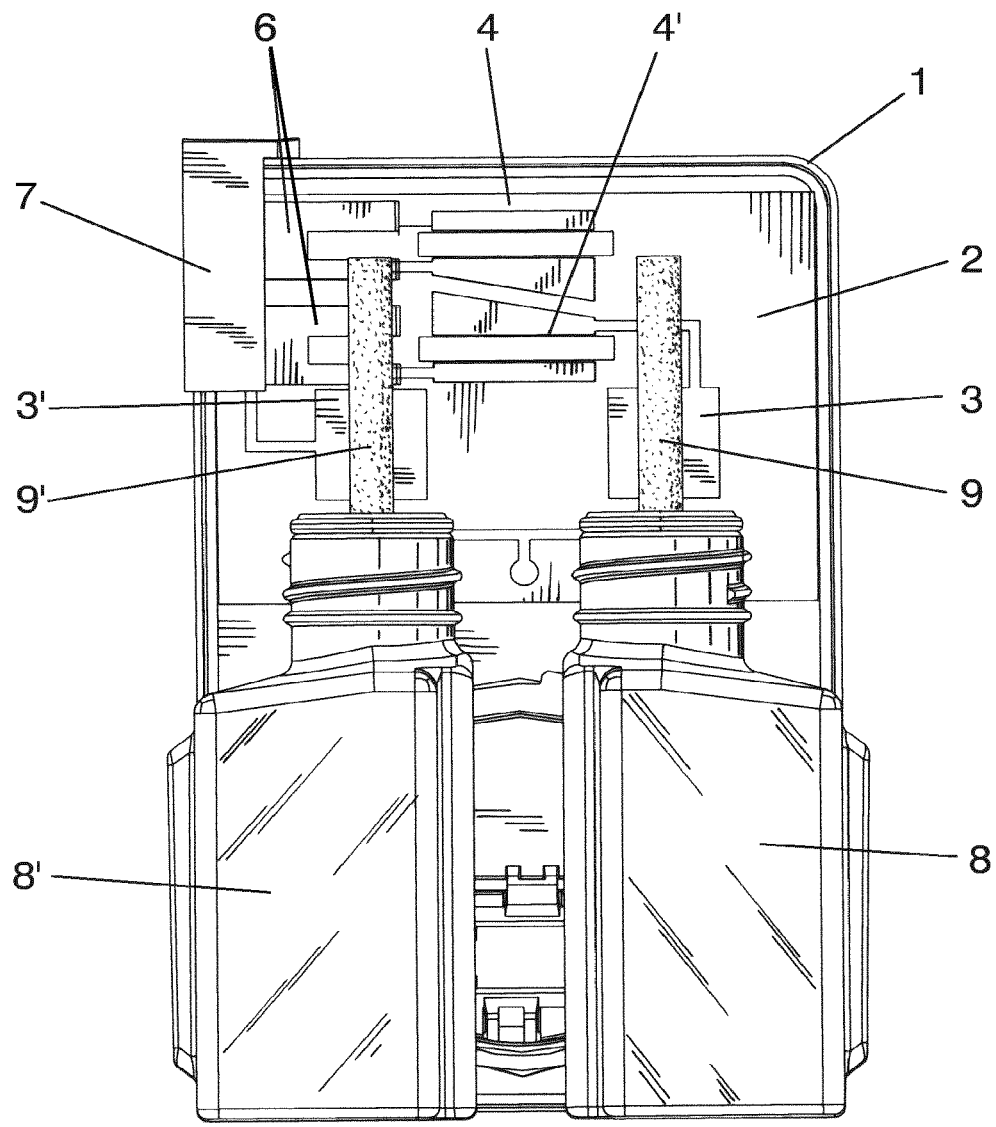
FIG. 5.—shows two perspective views (a,c) and one front elevational view (b) of another multifragrance embodiment of the invention.
Figure 5B:
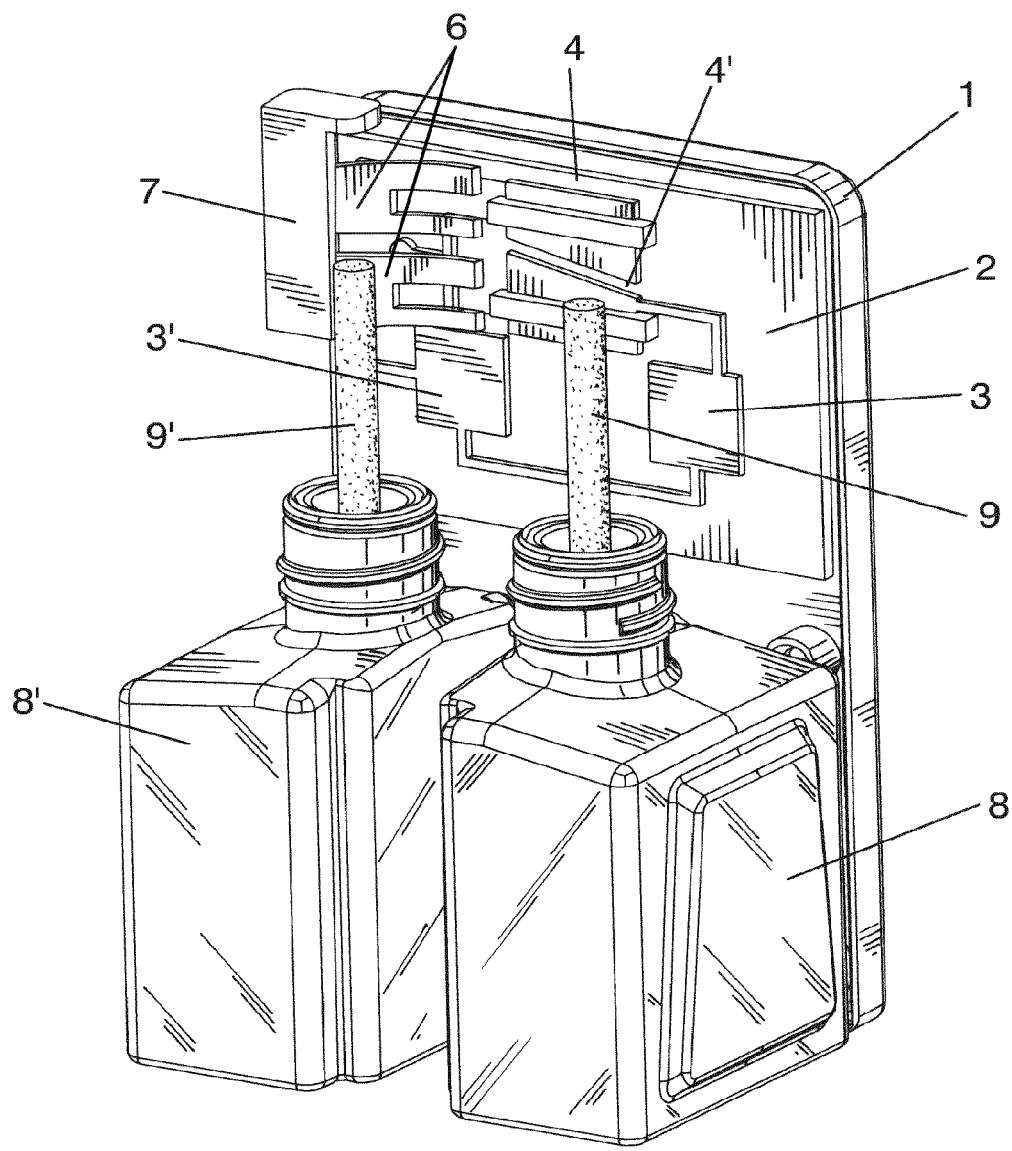

FIG. 5 also shows a multifragrance emission device, but in this case with simultaneous evaporation of two perfumes so that the two perfumes are mixed.

In this embodiment, the device comprises: two wicks (9,9') and associated containers, two corresponding heating resistors (3,3'), two potentiometers (4,4'), and two separating walls (11,11'). A single cursor (6) is provided in common for regulating the resistive value of the two potentiometers (4,4'), which in this case, are arranged one above the other, so that the cursor (6) slides simultaneously on all the tracks (5,5',5",5'") of the two potentiometers, so that it sets a resistive value for the two potentiometers.

The effect of the embodiment of FIG. 5, is that while the cursor move from left to right, emanation of fragrance evolves from 100% of a first perfume to 100% of a second perfume, with all possible intermediate positions (intermediate mixture of perfumes).

Also, it is possible to identify certain positions as labelled perfumes.

The invention claimed is:

1. An electrical heating device for evaporating volatile substances with adjustable evaporation rate, comprising
    two wicks and two associated containers;
    two corresponding heating resistors arranged in the device for heating a volatile substance upon being supplied an electric current;
    a solid substrate incorporating a first and a second potentiometer, wherein said first and second potentiometers:
        are electrically associated with said heating resistors for regulating the electric current passing through the resistor for manually regulating the evaporation rate,
        are arranged side by side, and
        are made of the same material as the heating resistors,
        are planar potentiometers, each having two conductive tracks and a cursor arranged for sliding along said tracks connecting them, wherein each of the two conductive tracks has a base track and a main track made of the same material, each base track being thicker or wider than each main track, and each main track having the same resistive value as the heating resistors,
        wherein said conductive tracks are formed on one surface of a printed circuit board; and
    a first separating wall arranged between the two conductive tracks of the first planar potentiometer, and a second separating wall arranged between the two conductive tracks of the second planar potentiometer, each separating wall for physically isolating the respective conductive tracks.

2. The electrical heating device according to claim 1, wherein said printed circuit board is made of a porous material, said printed circuit board being in contact with a liquid volatile substance, in such a manner that the printed circuit board conveys the volatile substance close to the heating resistor to enhance its evaporation.

3. The electrical heating device according to claim 1, wherein said heating resistor is mounted on a surface of said printed circuit board, and is electrically connected with said planar potentiometer.

4. The electrical heating device according to claim 3, wherein the heating resistor and the planar potentiometer are mounted on the same surface of the printed circuit board.

5. The electrical heating device according to claim 1, wherein said conductive tracks are covered by an electrical conductive protective lacquer, to protect the tracks from chemical attack of the evaporated volatile substance.

6. The electrical heating device according to claim 1, wherein separation means are arranged between the two conductive tracks of the first potentiometer and between the two conductive tracks of the second potentiometer, in order to avoid formation of a continuous film of the volatile substance between the two tracks.

7. The electrical heating device according to claim 6, wherein said separation means comprise an elongated hole perforating the printed circuit board in between said tracks for physically isolating the tracks.

8. The electrical heating device according to claim 6, wherein said separation means comprise a separating wall provided protruding from the printed circuit board in between said tracks for physically isolating the tracks.

9. The electrical heating device according to claim 2, wherein the width and/or the thickness of one of the tracks progressively increases from a first end of the track to a second end, so that said track's resistive value progressively increases from the first end to the second end.

10. The electrical heating device according to claim 1, wherein the volatile substance carrier comprises a wick having one end immersed in a liquid volatile substance including a perfume and/or insecticide active substance inside a container, whereas another end of the wick protrudes from the container and it is arranged to be heated by a heating resistor.

11. The electrical heating device according to claim 1, further comprising: a single cursor provided in common for regulating the two potentiometers' resistive value, so that the cursor slides only on the tracks of one potentiometer at a time to set a resistive value only for one potentiometer, whereas the other potentiometer is open.

12. The electrical heating device according to claim 1, further comprising: a single cursor provided in common for regulating the two potentiometers' resistive value, so that the cursor slides simultaneously on all the tracks of the two potentiometers, so that it sets a resistive value for the two potentiometers.

* * * * *